(12) United States Patent
Franci et al.

(10) Patent No.: US 9,707,410 B2
(45) Date of Patent: Jul. 18, 2017

(54) PIERCE AND FILL DEVICE

(75) Inventors: Xavier Franci, Loncin (BE); Philippe Dumont, Loncin (BE); Svein-Erik Lindgaard, Oslo (NO)

(73) Assignee: General Electric Company, Schenectady, NY (US)

( * ) Notice: Subject to any disclaimer, the term of this patent is extended or adjusted under 35 U.S.C. 154(b) by 315 days.

(21) Appl. No.: 13/882,392

(22) PCT Filed: Nov. 1, 2011

(86) PCT No.: PCT/US2011/058742
§ 371 (c)(1),
(2), (4) Date: Apr. 29, 2013

(87) PCT Pub. No.: WO2012/061359
PCT Pub. Date: May 10, 2012

(65) Prior Publication Data
US 2013/0225903 A1    Aug. 29, 2013

Related U.S. Application Data

(60) Provisional application No. 61/408,917, filed on Nov. 1, 2010.

(51) Int. Cl.
*A61B 19/00*      (2006.01)
*A61N 5/10*      (2006.01)
(Continued)

(52) U.S. Cl.
CPC ............ *A61N 5/1007* (2013.01); *A61M 5/002* (2013.01); *B65B 3/003* (2013.01); *B65B 39/04* (2013.01);
(Continued)

(58) Field of Classification Search
CPC ........ A61J 1/2089; A61J 1/201; A61J 1/2096; A61N 5/1007; A61M 5/002; A61M 5/162; B65B 3/003; B65B 39/04
(Continued)

(56) References Cited

U.S. PATENT DOCUMENTS

| | | |
|---|---|---|
| 3,406,686 A | 10/1968 | Keller |
| 4,523,679 A | 6/1985 | Paikoff et al. |

(Continued)

FOREIGN PATENT DOCUMENTS

| | | |
|---|---|---|
| EP | 0961608 B1 | 4/2003 |
| EP | 1272238 B1 | 8/2005 |

(Continued)

OTHER PUBLICATIONS

PCT/US2011/048742 ISRWO Dated Feb. 16, 2012.
(Continued)

*Primary Examiner* — Philip R Wiest

(57) ABSTRACT

A pierce and fill connector cap for a vial sealed by an elastomeric septum includes a vial collar and a needle holder. The vial collar body defines a collar aperture to be positioned in overlying registry with the septum of the vial, and the needle holder includes a needle holder body providing a means for holding an elongate needle in registry with the collar aperture. The needle holder body being moveable with respect to said vial collar between a first position spaced from the vial collar and a second position proximate the vial collar, such that a needle held by the needle holder will puncture through the vial septum.

17 Claims, 11 Drawing Sheets

(51) Int. Cl.
  *B65B 3/00* (2006.01)
  *B65B 39/04* (2006.01)
  *A61M 5/00* (2006.01)
  *A61J 1/20* (2006.01)
  *A61M 5/162* (2006.01)

(52) U.S. Cl.
  CPC .............. *A61J 1/201* (2015.05); *A61J 1/2096* (2013.01); *A61M 5/162* (2013.01); *A61M 2005/1623* (2013.01)

(58) Field of Classification Search
  USPC .................................................. 604/403–416
  See application file for complete search history.

(56) References Cited

U.S. PATENT DOCUMENTS

| | | | |
|---|---|---|---|
| 4,639,250 A | | 1/1987 | Rycroft |
| 5,232,029 A | * | 8/1993 | Knox et al. ................... 141/329 |
| 5,411,480 A | | 5/1995 | Kriesel |
| 5,429,614 A | * | 7/1995 | Fowles ................. A61J 1/2089 604/201 |
| 5,766,147 A | * | 6/1998 | Sancoff et al. ............... 604/520 |
| 5,989,237 A | * | 11/1999 | Fowles ................. A61J 1/2089 604/413 |
| 6,209,738 B1 | * | 4/2001 | Jansen et al. ................. 215/247 |
| 6,626,862 B1 | | 9/2003 | Duchon et al. |
| 6,994,213 B2 | | 2/2006 | Giard, Jr. et al. |
| 7,734,331 B2 | | 6/2010 | Dhawale et al. |
| 8,172,824 B2 | * | 5/2012 | Pfeifer ................. A61J 1/2089 604/411 |
| 8,562,582 B2 | * | 10/2013 | Tuckwell .............. A61J 1/2096 138/162 |
| 2003/0230521 A1 | | 12/2003 | Schick |
| 2011/0094619 A1 | | 4/2011 | Steel et al. |

FOREIGN PATENT DOCUMENTS

| | | |
|---|---|---|
| EP | 1287804 B1 | 2/2012 |
| EP | 2049062 B1 | 6/2013 |
| JP | 60-222059 A | 11/1985 |
| JP | 07-184979 A | 7/1995 |
| JP | 2001-511056 A | 8/2001 |
| JP | 2003126221 A | 5/2003 |
| JP | 2009-160419 A | 7/2009 |
| JP | 2009538213 A | 11/2009 |
| JP | 2005-324007 A | 6/2010 |
| WO | 9927886 A1 | 6/1999 |
| WO | 03057289 A1 | 7/2003 |
| WO | 2007140238 A2 | 12/2007 |
| WO | 2008067467 A2 | 6/2008 |
| WO | 2009100428 A1 | 8/2009 |
| WO | 2010022870 A1 | 3/2010 |

OTHER PUBLICATIONS

EP Search Report dated Mar. 16, 2015; 9 pages.
First Chinese Office Action and Search Report dated Nov. 4, 2014; 6 pages.
English Translation of First Chinese Office Action and Search Report dated Nov. 4, 2014.
Extended European Search Report with a mail date of Sep. 15, 2015; 17 pages.

* cited by examiner

PIERCE AND FILL DEVICE

FIELD OF THE INVENTION

The present invention relates to the field of dispense and fill devices. More specifically, the present invention is directed to a piercing device for a fluid container which allows piercing of a container stopper or septum while the container is still within a container or bag so as to maintain the sterility of the fluidpath of a dispenser for filling the container.

BACKGROUND OF THE INVENTION

For most dispensing solutions of a Positron Emission Tomography (PET) tracer, a bulk tracer solution needs to be divided into several fractions. Such dispensing needs to be done under aseptic conditions, typically Class A clean room with class B background. The operations for these PET tracers, as the tracers are radioactive, are desirably conducted in a fully-automated manner within shielded cells.

Most PET tracer manufacturing sites have limited number of hot-cells with class A clean room environment. Therefore a means enabling aseptic filling in class C environment would expand the potential PET production sites that could produce the tracers. Additionally, enabling any PET tracer manufacturing site to dispense in aseptic condition within a clean room class C may be the basis for a new dispenser to be provided to a wider market (beyond tracer production centers having clean room dispensing facilities).

WO2009/100428 discloses a way to dispense aseptically fluids in a closed sterile disposable fluid path (called disposable kit) allowing thus this operation to be performed in a clean room class C whilst dispensing is usually performed in clean room class A environment. Within the disposable kit, the connection between the closed sterile vial and the fluid path is ensured by a needle piercing the vial stopper.

A pre-piercing of the stopper during assembly of the disposable kit in the factory may not be an appropriate solution for sterile connection. Indeed aging of the assembly between the time the kit was assembled and the time it is used for dispensing may lead to leaks at the piercing holes, thus compromising sterility of the connection.

There is therefore a need in the art for a means of connecting dispense vial to a dispense cassette closer to the time of dispense cassette use. There is also a need in the art for a means of connecting the dispense vial to the dispense cassette while both are still within a container or bag maintaining a sterile environment for the surfaces which will conduct a pharmaceutical product.

DETAILED DESCRIPTION OF THE PREFERRED EMBODIMENTS

Figure 1:
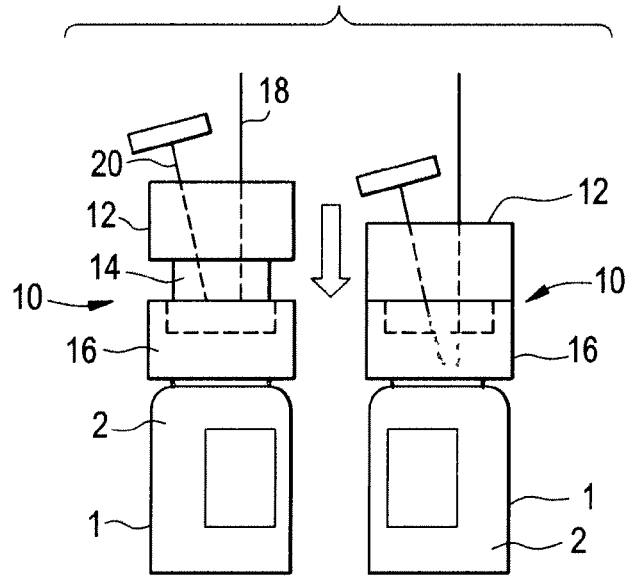
FIG. 1 depicts a pair of piercing devices of the present invention, one in a first position maintaining a fill and vent needle away from a container stopper, the other in a second position in which the fill and vent needle both pierce a container stopper.

In view of the needs of the prior art, the present invention discloses a device and method for connecting a dispense needle of a sterile dispense cassette and a closed sterile vial just before use, when both items are still sterile in a plastic bag or container.

The present invention, called a "snap and pierce" device or a "connector cap" allows one or more needles to pierce a stopper of a closed sterile vial in a safe manner while still inside a sterile bag. The device will allow the operator to pierce the stopper just before opening the sterile bag, ensuring therefore the piercing in sterile condition and also keeping the leak-tightness properties of the stopper as it may thus be pierced only minutes before its usage.

The present invention includes a vial hermetically-closed (with a rubber stopper or septum) and a snap-and-pierce cap (or piercing device) containing one or more needles maintained on the top of the vial. The piercing device of the present invention is desirably formed of a polymeric material suitable for dispensing radioactive pharmaceutical fluids. One of the needles is connected to a sterile gas 0.22 μm liquid filter (to filter the incoming liquid, e.g. the drug product), the other needle, when gas venting is required, is connected to a sterile 0.22 μm gas filter (filter used to vent the vial). The two filters may be connected directly onto the snap-and pierce cap or may be part of the fluid path (tubes, stopcock manifolds, etc.) connected to the snap-and-pierce cap. Typically, the 0.22 μm sterile gas filter is directly connected to the snap-and-pierce cap (or at least in direct fluid communication with the vial cavity) while the 0.22 μm liquid filter is part of the fluidpath connected to the snap-and-pierce cap (i.e. the filter is connected to the stopcock manifold part of the disposable dispensing kit).

All items are sterilized and sealed within a bag to ensure sterile storage. To connect the vial to the filters, the snap-and-pierce cap is punched onto the stopper of the vial enabling penetration of the needles into the vial through its stopper. This operation is done while all items are still in the sterile bag. The bag may further include a plastic tray holding each component in formed depressions and which includes a deflectable blister for each cap of the present invention so as to facilitate this operation.

Thus the whole kit is assembled, then inserted in a plastic bag, suitable for sterile packaging, than sealed in appropriate clean room class and then sterilized (e.g. sterimization through gamma irradiation but other sterilization means may also be used). The "snap and pierce" device stay unpierced until the operator on dispensing site punches the needles through the stoppers while the whole dispensing kit is still in the sealed plastic bag. Because the disposable dispensing kit and the "snap and pierce" device is inside the plastic bag, this operation is performed in aseptic environment whatever the class environment the operator is in.

Once this connection is made, ie, once the device is actuated to pierce the septum of the associated vial, the bag can be opened without compromising sterility of the vial as inlet and outlet are protected through 0.22 μm filters.

The device may consist in several vials equipped with the pierce and snap cap and a system allowing to punch all the caps at once on their respective vials.

Figure 2:
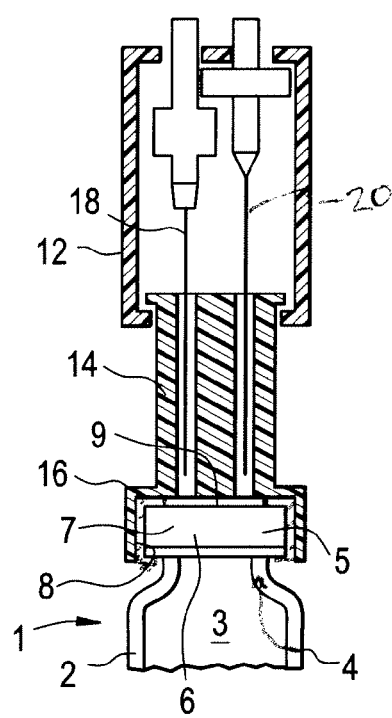
FIG. 2 depicts a piercing device of the present invention which accommodates a fill needle and a vent needle which extend substantially in parallel alignement to each other.
Figure 3:
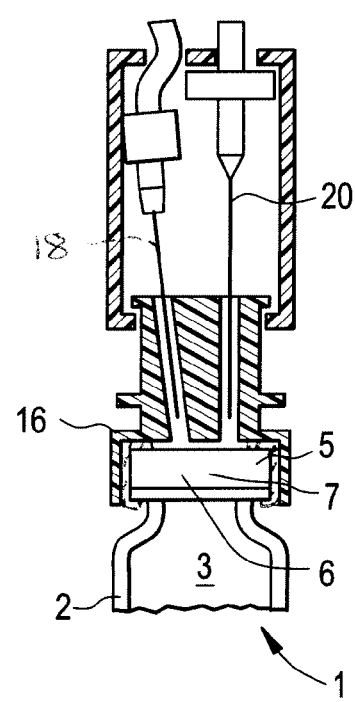
FIG. 3 depicts a piercing device of the present invention which accommodates a fill needle and a vent needle which extend in non-parallel aligment with each other.
Figure 4:
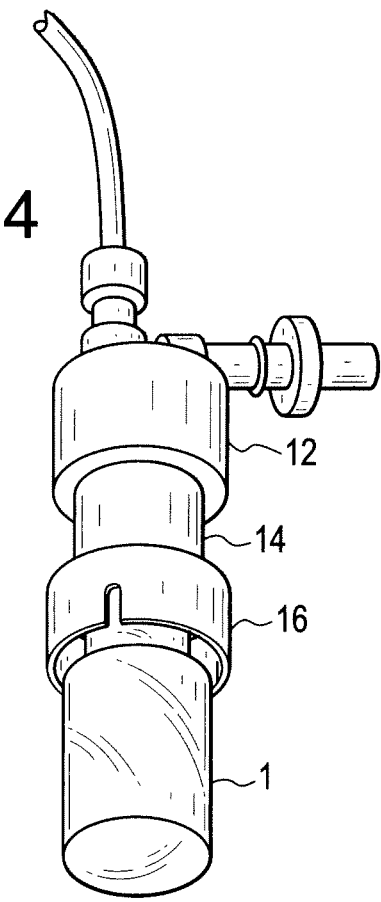
FIG. 4 depicts a piercing device of the present invention assembled to a vial.
Figure 5:
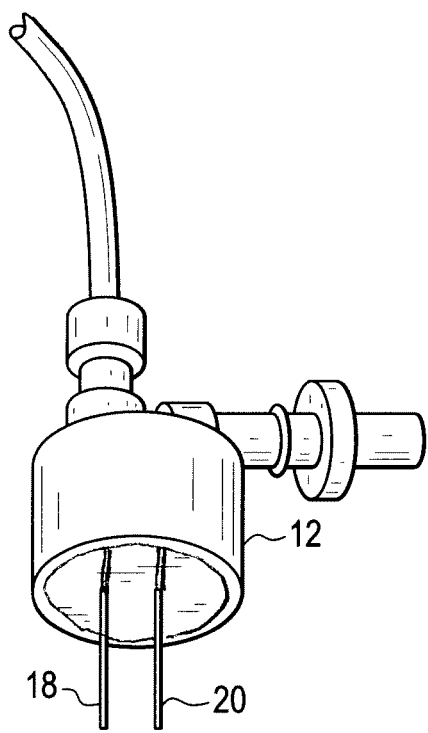
FIG. 5 depicts the needle cap, or needle holder, of the piercing device of FIG. 4.
Figure 6:
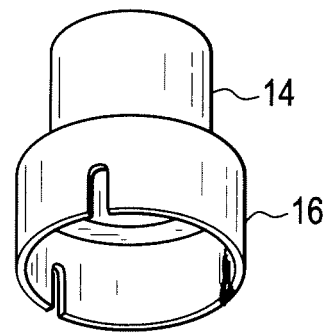
FIG. 6 depicts the piercing guide and vial collar of the piercing device of FIG. 4.

Referring to FIGS. 1-3, the present invention provides a piercing device 10 for penetrating a sealed container 1 at the appropriate time prior to filling the container. Container 1 includes a vial body 2 defining a vial cavity 3 and having an upstanding annular neck 4 and an outwardly-protruding annular rim 5. Annular neck 4 defines a vial aperture 6 in open fluid communication with vial cavity 3. An elastomeric septum 7 spans across aperture 6 so as to seal cavity 3 from the outside environment. Septum 7 may be adhered to vial neck by any conventional means such as by compatible adhesives or by interference fit with neck 4 either about rim 5 or within aperture 6 (as per a vial stopper). As seen in FIGS. 2 and 3, container 1 may further include an annular metallic crimp 8 for mechanically securing septum 7 across aperture 6. Crimp 8 includes a central aperture 9 in open overlying registry with septum 7 so as to expose septum 7 for piercing by one or more needles for filling into and/or dispensing from cavity 3.

As shown in FIG. 1, piercing device 10 includes a needle holder 12, a piercing guide 14, and a vial collar 16. Needle holder 12 maintains the needles in place and enables connection to the filters and the fluidpath (filters may be directly connected to the needle holder or be part of the fluidpath connected to the needle holder) to piercing device 10. Piercing guide 14 holds the needles away from the stopper until moved to the second position, and also guides the needles for a proper septum piercing. Vial collar 16 ensures the device is tightly connected onto the top of the sterile vial. Needle holder 12 is shown with a fill needle 18 and a vent needle 20 fixed to extend therethrough in overlying registry with septum 7 of container 1. In a first position, needle holder 12 maintains needles 18 and 20 in spaced separation from septum 7. As also shown in FIG. 1, needle holder 12 may be moved along piercing guide 14 to a second position, such that the free ends 18a and 20a of needles 18 and 20 pierce through septum 7 so as to extend into cavity 3 of container 1. Each of needles 18 and 20 typically include elongate cannulas 22 and 24 supported by a base luer 26 and 28, respectively.

With additional reference to FIGS. 2-6, piercing guide 14 and vial collar 16 may be formed either as separate components which are mated together, or as a single component which provides both functions. When formed as separate components, the present invention contemplates both piercing guide 14 and vial collar 16 may be removable from container 1 so that, after filling, container 1 will be free of all components of the present invention. Alternatively, vial collar 16 may remain with container 1 after is removed therefrom. Vial collar 16 may thus be removably snapped into position about neck 4 of container 1 by deflection of vial collar 16. Similarly, when piercing guide 14 is not affixed to vial collar 16, piercing guide may be removably attached thereto by means such as an interference fit, a bayonet-type connection, threaded connection, etc. Desirably, the present invention contemplates that needle holder 12 will be affixed to piercing guide 14 once moved to the second position so that needle holder 12 would be removed from container with piercing guide 14, whether with vial collar 16 or not. That is, the present invention contemplates that it will be far easier to remove either piercing guide 14 from vial collar 16 or vial collar 16 from the neck of the container than to remove needle holder 12 from piercing guide 14.

Additional details of piercing device 10 are described hereinbelow.

Figure 7:
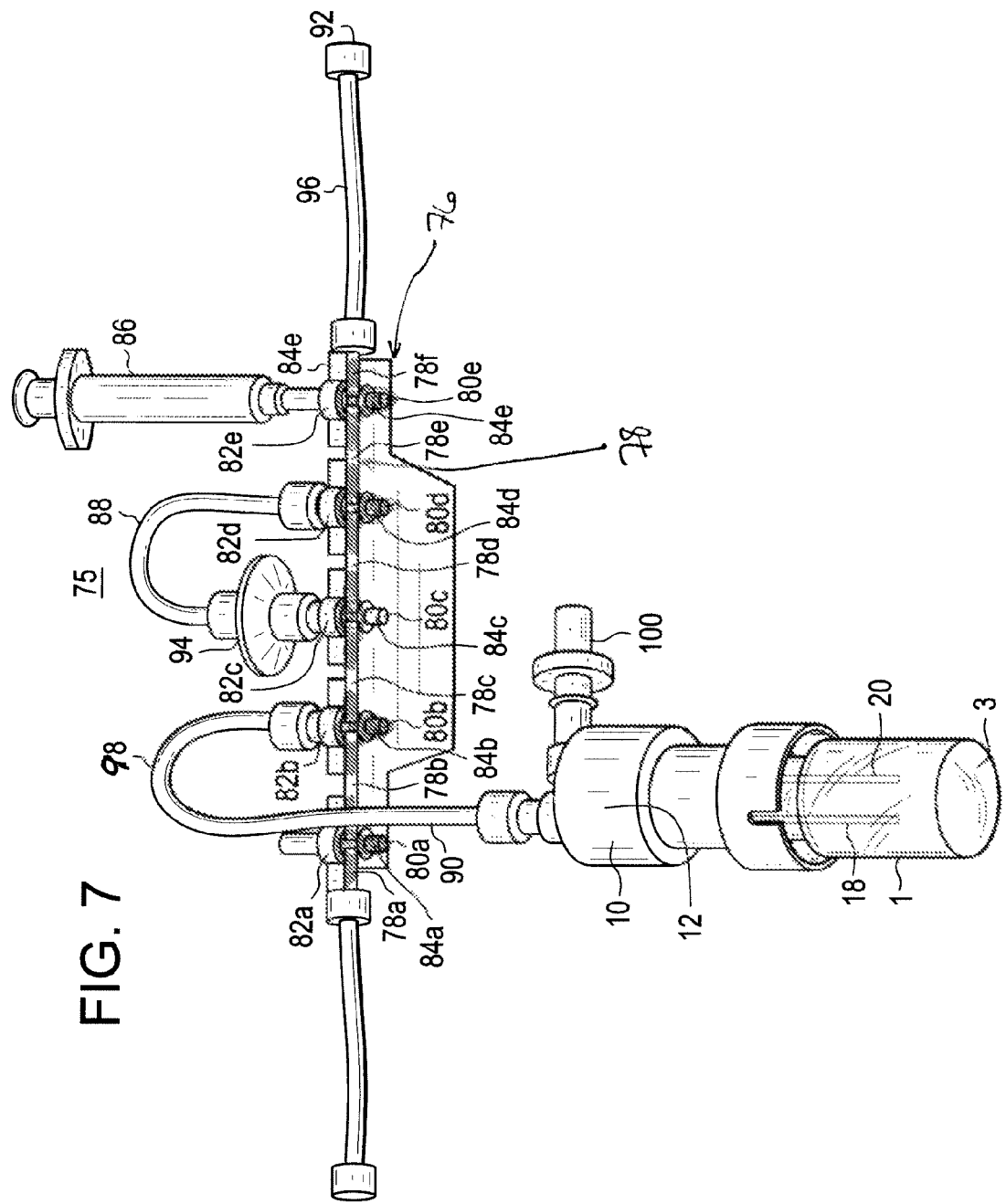
FIG. 7 depicts the piercing device and vial of FIG. 4 assembled to a dispense manifold.
Figure 8:
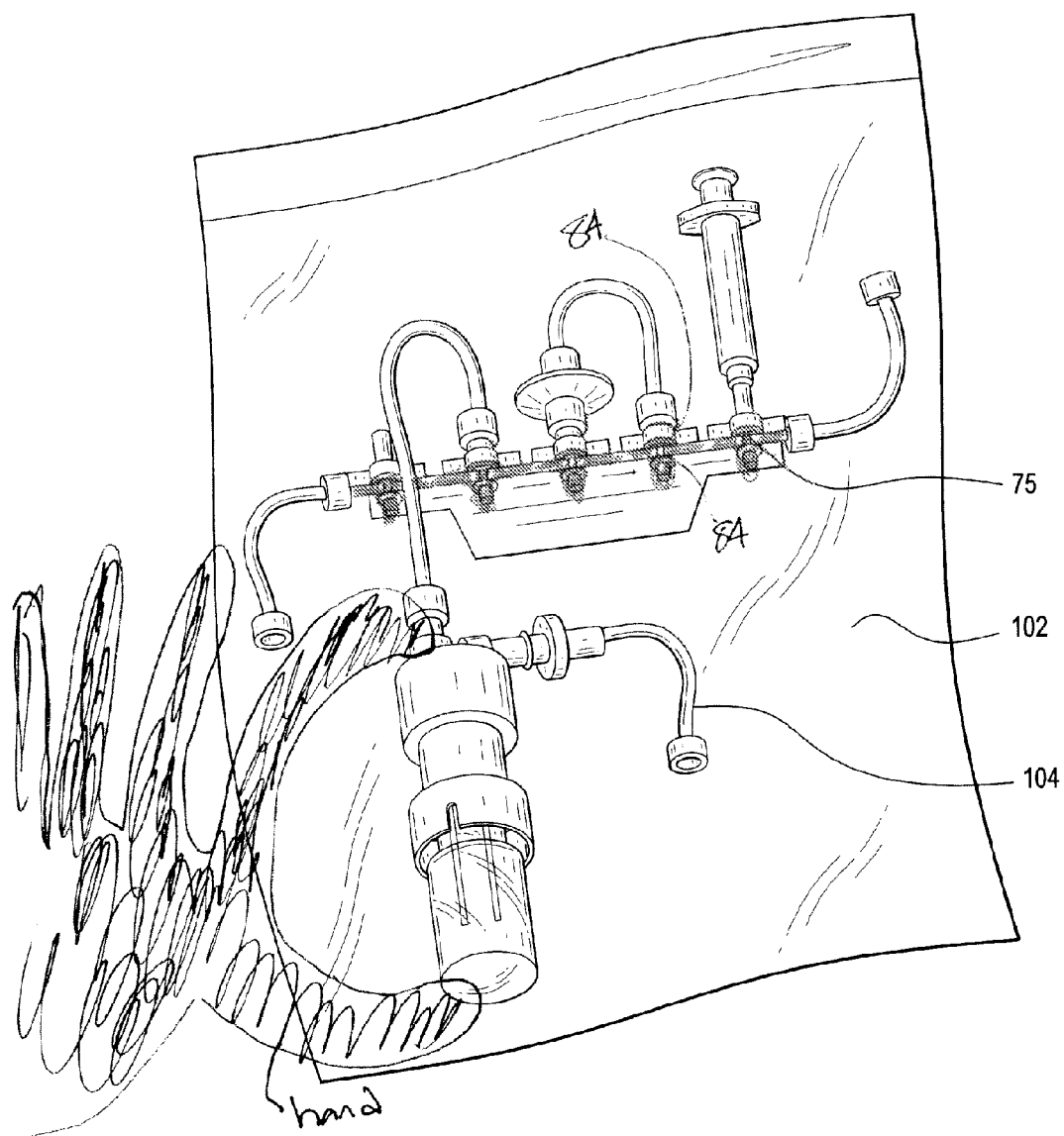
FIG. 8 depicts the piercing device, vial and dispense manifold of FIG. 7 within a sealed container and the ability to manipulate the piercing device through the container wall.
Figure 9:
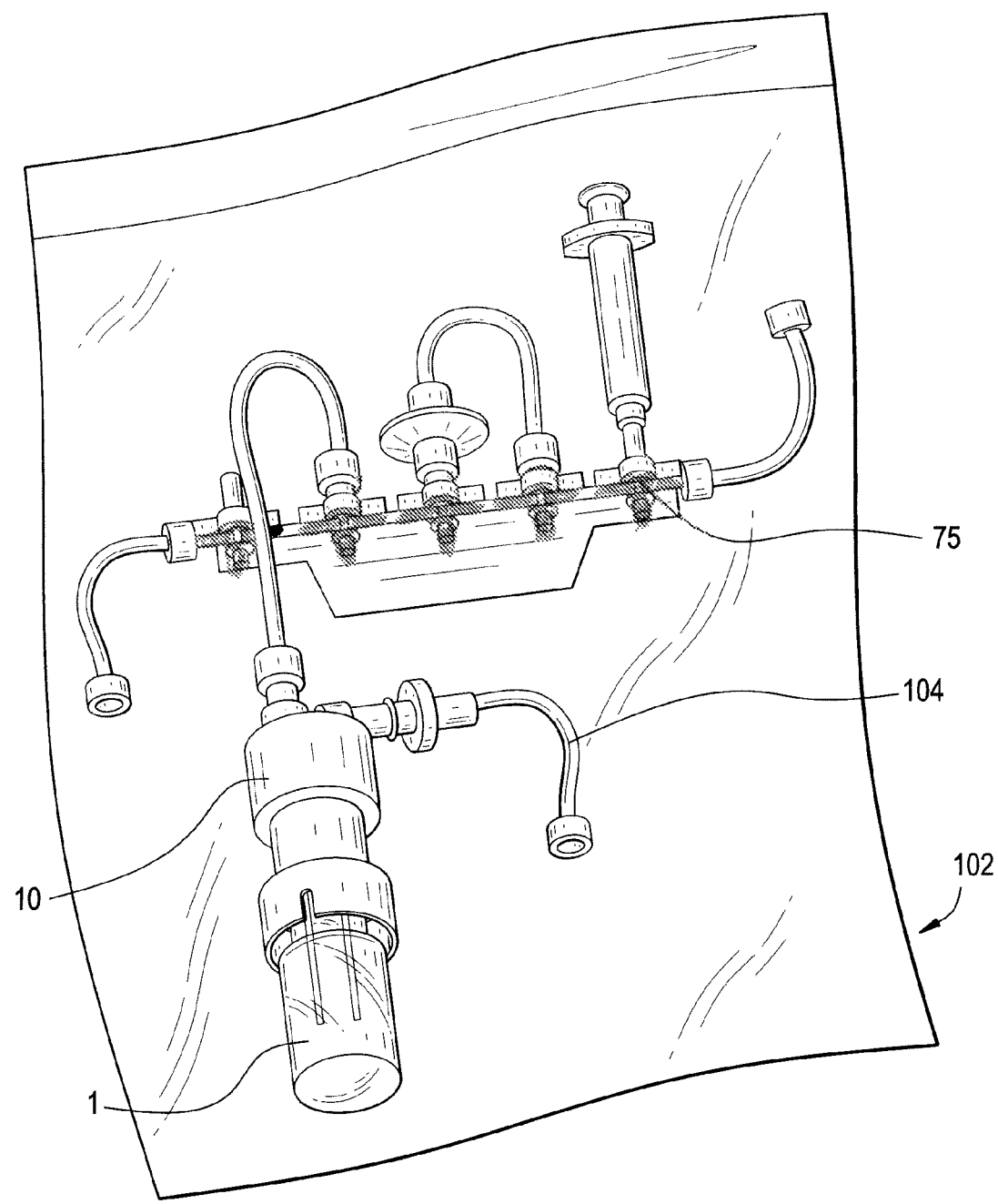
FIG. 9 depicts the piercing device, vial and dispense manifold of FIG. 8 after the piercing device has been activated to the second position, so that the flowpath of the dispense manifold is now sealed and the sterility of the flowpath maintained prior to opening the container.

Referring now to FIGS. 7-9, the present invention contemplates that piercing device 10 may be incorporated into a dispense cassette 75 for container 1. Dispense cassette 75 includes a manifold body 76 defining co-axially aligned passageway segments 78a-f of a passageway 78, a number of valve sockets 80a-e along passageway 78, each valve socket in fluid communication with both flowpath 78 and a unique conduit 82a-e, also defined by manifold body 76. A valve 84a-e is positioned in each valve socket 80a-e, respectively. Dispense system further includes a syringe pump 86 positioned in sealed fluid communication with conduit 82e, a filter conduit 88 extending in sealed fluid communication between conduits 82c-d, and a dispense conduit 90 extending to piercing device 10, all for directing flow from a source input 92 to a container 1. Filter conduit 88 supports a filter 94 thereon. Filter 94 is desirably a dead-end filter which filters a source fluid from conduit 80d into a cleaner filtrate flowing into conduit 82c. A dead-end filter is sufficient when dispense cassette 75 is used as a single-use system and even for most dispenses should it be re-used. Filter 94 desirably provides a 0.22 micron filter although the filter specifications may be selected as desired for the particular operation. Dispense cassette 75 thus provides a feed flowpath 96 through which a source fluid flows from an exterior fluid source to filter 94. Dispense cassette 75 also provides a filtrate flowpath 98 leading from filter 94 to at least one product dispense vial 1. Feed flowpath 96 comprises passageway segment 78f, conduit 82e, syringe pump 86, passageway segment 78e, conduit 82d, and filter conduit 88. Filtrate flowpath 98 extends from filter 94 through conduit 82d, segment 78c, conduit 82c, and dispense conduit 90. Feed flowpath 96 is thus in filtered fluid communication with filtrate flowpath 98 through filter 94.

Dispense conduit 90 connects to fill needle 18 supported in needle holder 12 of piercing device 10. When needle holder 12 is moved into the second position, filtrate flowpath 98 will be in sealed fluid communication with cavity 3 of container 1. Vent needle 20 is also supported by needle holder 12 such that a first end will pierce into cavity 3 while the second end will be in sealed fluid communication with another filter 100 which would thus maintain the sterile integrity of cavity 3 and filtrate flowpath 98. The vent filter allows any entrapped gas within cavity 3 to escape while still maintaining the product filtrate fluid within container 1. Vent needle 20 typically includes an elongate hollow vent conduit body supporting a filtration media therein, or in sealed fluid communication therewith, for allowing air to vent from cavity 3 while maintaining the controlled environment thereof. It is further contemplated by the present invention that filters may also be positioned at each end of manifold body 76 so as to maintain the sterile integrity of all flowpaths and passageways of dispense cassette 75. In this manner, dispense cassette 75 may be connected together in an environmentally-controlled environment, desirably a sterile or a GMP-compliant environment, so that all of the fluid flowspace beyond filter 94 continues to meet the standards of the controlled environment. Desirably, a Class A environment is provided and maintained by the present invention. When dispense cassette 75 is manufactured in such a sterile manner, it may be placed into and sealed within the containment cavity 104 of a containment bag 102 so as to maintain the sterility of at least dispense flowpath 98. Additionally, the present invention contemplates that piercing device 10 may be included in bag 102 with both fill needle 18 and vent needle 20 held by needle holder 12 in the first position.

As shown in FIGS. 8 and 9, an operator may then manipulate piercing device 10 through bag 102, prior to containment bag 102 being opened, so that needle holder 12 will be in the second position and thus allow dispensing into container 1. The septum 7 of container 1 may thus be pierced shortly before dispense system is removed from bag 102 and used to fill container 1, thereby minimizing the time that septum 7 is pierced prior to filling.

Syringe pump 86 may be manually, electrically or pneumatically controlled to draw a source fluid from a source connected at source input 92 and to then expel the source fluid back out. Valve 84e provides selectable fluid communication between pump 86 and either source input 92 or passageway segment 78f and thus filter 94.

Dispense cassette 75 is desirably operated by a PLC controller (not shown) for selectively operating syringe pump 86 and valves 84e-f so as to direct fluid from fluid source 92 to container 1. For convenience, associated electrical connections from the controller are not shown. Thus, dispense cassette 75 may include connectors for mating with an exterior controller or hardware platform which provides appropriate actuation of the pump and valve elements thereof.

Figure 10:
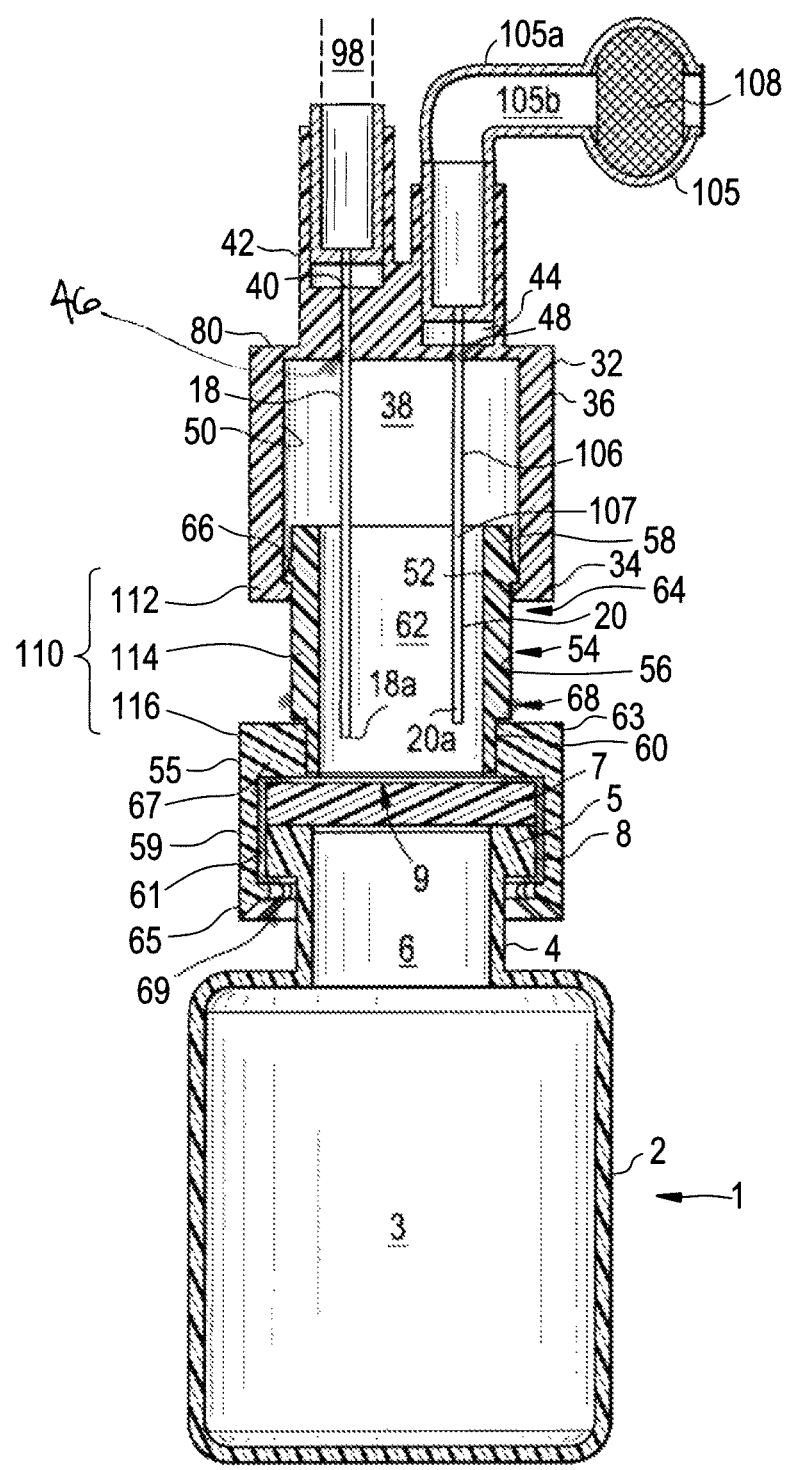
FIG. 10 depicts a dual-needle piercing device of the present invention in the first, pre-pierced, position.
Figure 11:
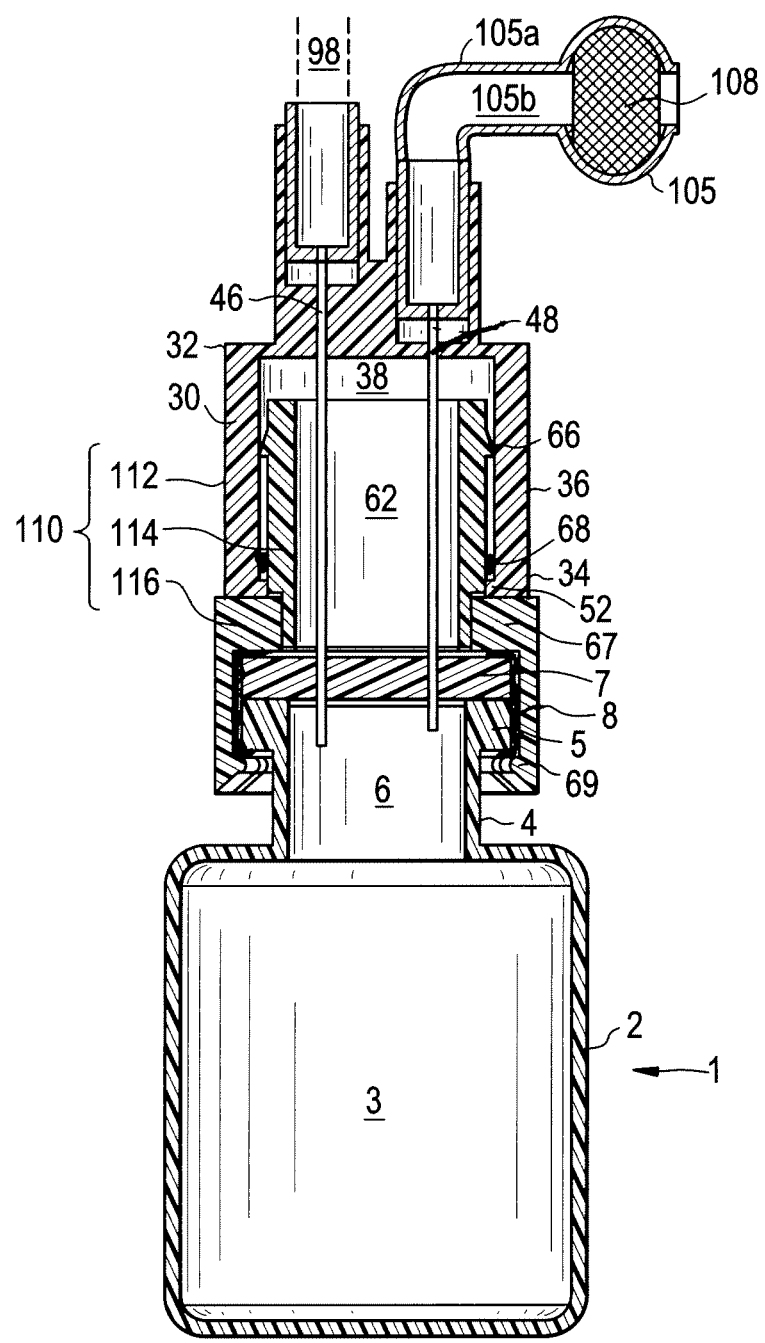
FIG. 11 depicts the piercing device of FIG. 10 in the second, piercing, position.

Additional reference is now made to FIGS. 10 and 11, showing device 110 in the first, pre-pierced, position and the second, piercing, position, respectively. Device 110 accommodates a first fluid fill needle 112 and a second gas vent needle 114. Gas vent needle 114 includes an elongate tubular body 106 defining an elongate open needle passageway 107 therethrough. Vent needle either supports or is positioned to be connected to a gas filter 105. Gas filter 105 includes a filter body 105a defining a filter passageway 105b. A porous filter media 108 spans filter passageway so that gas may vent therethrough from cavity 3. Needle passageway 107 thus extends in sealed fluid communication with filter passageway 105b such that gas may be vented from cavity 3 through filter media 108. Vent needle 20 includes a free end 20a which extends into cavity 3. Desirably, vent needle 20 is of a length which ensures that free end 20a passes through septum 7 into cavity 3 only as far as needed to ensure that gas trapped within cavity 3 may escape therethrough during filling operations. Fill needle 18, conversely, includes a free end 18a which may extend further into cavity 3 than free end 20a of vent needle 20.

Piercing device 110 includes a needle holder 112, a piercing guide 114, and a vial collar 116. Needle holder 112 maintains the needles in place and enables connection to the filters and the fluidpath (filters may be directly connected to the needle holder or be part of the fluidpath connected to the needle holder) to piercing device 110. Piercing guide 114 holds the needles away from the stopper until moved to the second position, and also guides the needles for a proper septum piercing. Vial collar 116 ensures the device is tightly connected onto the top of the sterile vial. Needle holder 112 is shown with a fill needle 18 and a vent needle 20 fixed to extend therethrough in overlying registry with septum 7 of container 1. In a first position, needle holder 112 maintains needles 18 and 20 in spaced separation from septum 7. As also shown, needle holder 112 may be moved along piercing guide 114 to a second position, such that the free ends 18a and 20a of needles 18 and 20 pierce through septum 7 so as to extend into cavity 3 of container 1.

Piercing guide 114 and vial collar 116 may be formed either as separate components which are mated together, or as a single component which provides both functions. When formed as separate components, the present invention contemplates both piercing guide 114 and vial collar 116 may be removable from container 1 so that, after filling, container 1 will be free of all components of the present invention. Alternatively, vial collar 116 may remain with container 1 after is removed therefrom. Vial collar 116 may thus be removably snapped into position about neck 4 of container 1 by deflection of vial collar 116. Similarly, when piercing guide 114 is not affixed to vial collar 116, piercing guide may be removably attached thereto by means such as an interference fit, a bayonet-type connection, threaded connection, etc. Desirably, the present invention contemplates that needle holder 112 will be affixed to piercing guide 114 once moved to the second position so that needle holder 112 would be removed from container with piercing guide 114, whether with vial collar 116 or not. That is, the present invention contemplates that it will be far easier to remove either piercing guide 114 from vial collar 116 or vial collar 116 from the neck of the container than to remove needle holder 112 from piercing guide 114.

Needle holder 112 includes an elongate needle holder body 30 having opposed closed end 32 and open end 34 and an open cylindrical wall 36 extending therebetween. Cylindrical wall 36 defines needle aperture 38 opening on open end 34. Closed end 32 includes transversely-extending needle surface 40. Surface 40 defines first and second needle receptors 42 and 44. Needle receptors 42 and 44 define first and second needle channels 46 and 48 for receiving fill needle 18 and vent needle 20, respectively. Desirably, needle receptors 42 and 44 include means for securely holding needles 18 and 20 with respect to body 30. By way of illustration and not of limitation, the means for securely holding needles 18 and 20 may be mechanical means which engage the needles, such as by interference fit or engagement mechanisms, or chemical means such as a suitable adhesive which secures one or both of the needles 18 and 20 and/or their luer bases 22 and 24, respectively. Luer base 22 of fill needle 18 is connected to dispense conduit 90 of dispense cassette 75. Luer base 24 of vent needle 20 is connected to vent filter body 105.

Needle receptors 42 and 44 define through-apertures 46 and 48 extending in open fluid communication with needle aperture 38. When fixed by needle receptors 42 and 44, needles 18 and 20 extend into and desirably through needle aperture 38. While needles 18 and 20 are shown to extend through aperture 38 and beyond open end 34 of needle holder 12, the present invention contemplates that the arrangement of needle holder 12, guide 14 and vial collar 16 with respect to each other such that the required penetration into or though needle aperture 38 of needles 18 and 20 may be appropriately varied. Cylindrical wall 36 includes an inwardly-facing cylindrical surface 50 and supports an inwardly extending detent 52 at open end 34. The present invention contemplates that detent 52 may be configured in a manner known in the art, such as an inwardly-extending annular rim or as a series of annularly-arrayed projections. As will be described hereinbelow, detent 52 will cooperate with a mating detent on the needle guide 14 so as to maintain needle holder in the first or second position as desired.

Piercing guide 14 includes a guide body 54 having an elongate cylindrical wall 56 extending between opposed first and second open ends 58 and 60, respectively. Wall 56 defines an open elongate guide passage 62 extending in open fluid communication between first and second open ends 58 and 60. Guide passage 62 is in fluid communication with needle aperture 38 and in underlying registry with through-apertures 46 and 48. Wall 56 includes an outer cylindrical surface 64 supporting mating detents 66 and 68 at first end 58 and second end 60, respectively. As previously described, mating detents 66 and 68 cooperate with detent 52 so as to maintain needle holder 12 in either the first or second position, as well as to allow an operator to move needle holder from the first position to the second position. Detents 66 and 68 are contemplated, like detent 52, to be either a single annular rim or an array of outwardly-extending projections. Furthermore, wall 56 may define an elongate linear channel extending between each of detents 66 and 68 so as to both ensure linear movement of needle holder 12 with respect to guide 14. Additionally, the present invention contemplates that needle holder 12 could support detents at opposed ends thereof, and piercing guide 14 only supports a single detent or array of detents at the first end thereof. Moreover, the present invention contemplates that both needle holder 12 and piercing guide 14 each support a pair of cooperating detents at both ends thereof to provide additional locking strength for maintaining needle holder 12 in the second position.

Vial collar 16 includes an annular collar body 55 defining a vial passageway 57 therethrough. Collar body 55 includes cylindrical wall 59, having an inwardly-facing cylindrical surface 61, extending between opposed first and second open ends 63 and 65. First open end 63 mates with second open end 66 of piercing guide 14. As previously noted, the present invention contemplates that vial collar 16 may be formed as a single unity with piercing guide 14 or as separate components which are either permanently fixed together. Additionally, vial collar 16 and piercing guide 14 may separably engage each other so that piercing guide 14 may be removed from engagement with vial collar 16. As shown in FIGS. 10 and 11, collar body 55 includes a first inwardly-extending annular rim 67 at first end 63. Rim 67 is configured to abut against the annular crimp 9 or with septum 7 of container 1. Additionally, cylindrical surface 61 supports an inwardly-extending annular detent 69 at second open end 71. Detent 69 engages the undersurface of annular rim 8 of container 1. Detent 69 is designed to deflect about rim 8 as vial collar 16 is positioned onto container 1. The present invention contemplates that detent 69 may take the form of a single annular rim, or an array of inwardly-extending projections, each of which will deflect sufficiently to be moveable past annular rim 8 as vial collar 16 is emplaced. Alternatively still, collar body 55 may include a number of axially-extending deflectable leafs on which the detents 69 are supported. The present invention contemplates that vial collar 16 may be removable from container 1 after a filling operation, or vial collar 16 may separate from device 10 so as to be transferable with container 1.

Needle holder 12 is thus movable from a first position, shown in FIG. 10, to a second position shown in FIG. 11. In the first position, detent 52 engages first detent 66 so as to maintain needles 18 and 20 away from septum 7 of container 1. In the second position, detent 52 is moved beyond detent 68 so as to maintain needles 18 and 20 through septum 7. In the second position, fill needle 18 places cavity 3 in fluid communication with filtrate flowpath 98 of dispense cassette 75. Additionally, in the second position, vent needle 20 places cavity 3 in fluid communication with the pores of filter media 108 so that gas may be vented during the fill operation.

After fluid dispensing has been completed, needles 18 and 20 are retracted back through septum 7 and container 1 may be removed from device 10. As previously described, device 10 may either be removed from engagement with vial collar 16 or piercing guide 14 may be disconnected from vial collar 16 (which remains attached to the vial). Device 10 has thus maintained septum integrity after attachment to container 1 until just prior to opening containment bag 102, when needle holder 12 has been moved to the second position so that needles 18 and 20 pierce septum 7. Filtrate flowpath 98 and cavity 3 will thus maintain the clean and sterile environment for dispensing a fluid into cavity 3. In this manner, device 10 provides a means for sterile dispensing in non-sterile environments.

Figure 12:
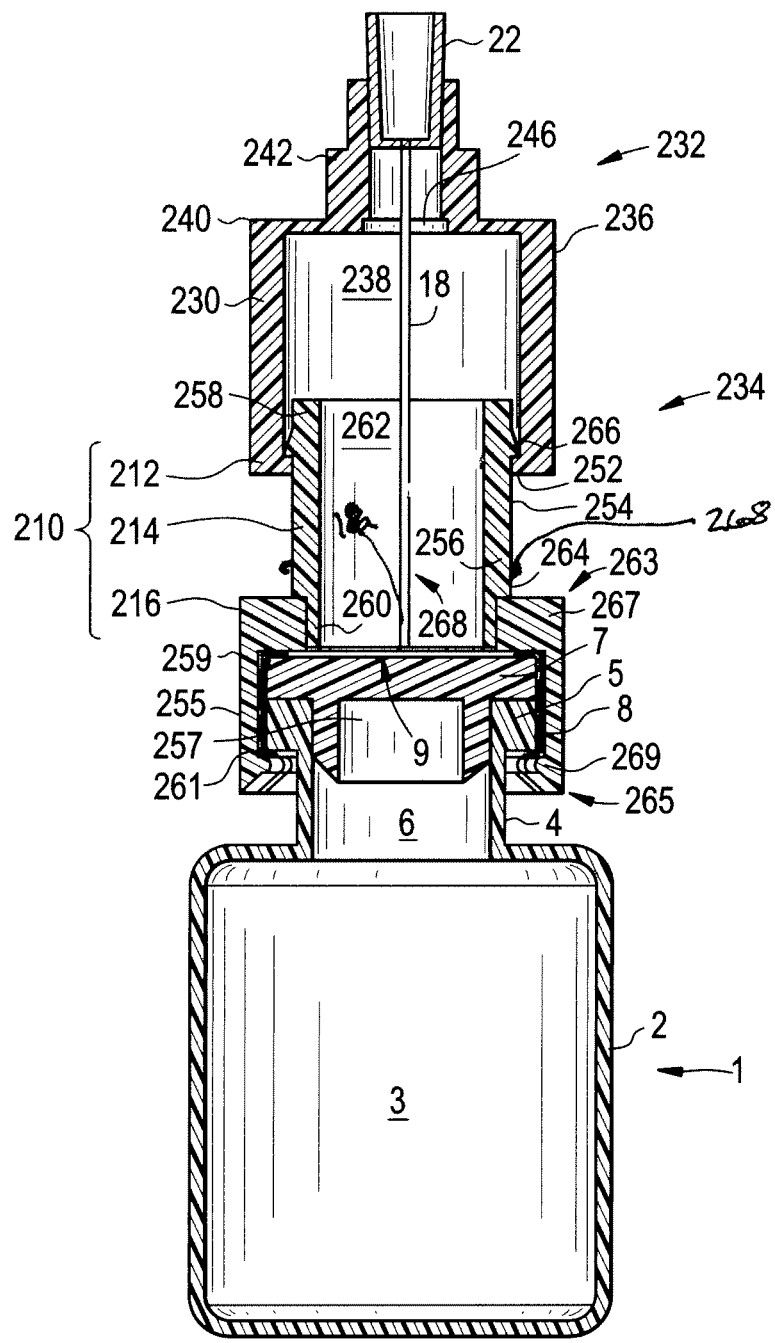
FIG. 12 depicts a single-needle piercing device of the present invention in the first, pre-pierced, position.
Figure 13:
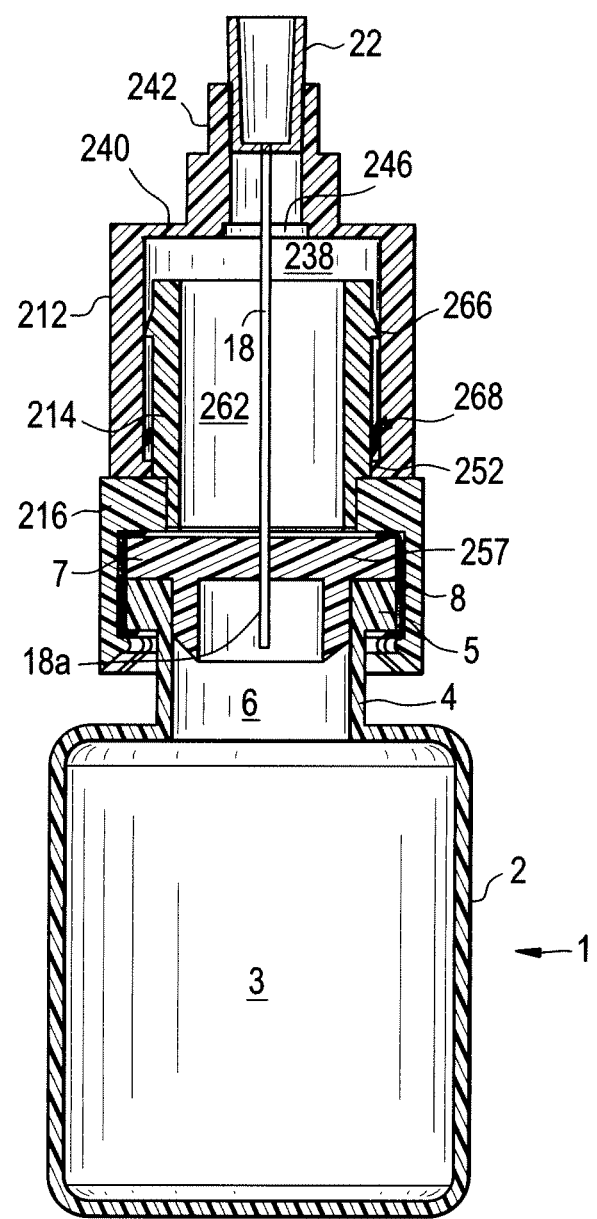
FIG. 13 depicts the piercing device of FIG. 12 in the second, piercing, position.

FIGS. 12 and 13 depict a single-needle piercing device 210 of the present invention in the first, pre-pierced, position and the second, piercing, position, respectively. Device 210 may be used when container 1 is formed with an evacuated cavity 3, such that there will be no gas to vent during fill operations and no need for a gas vent needle or filter. Device 210 provides the same ability to pierce the septum of a container while it is still within an outer container or bag. Device 210 can thus help maintain the sterility of the fluid flowpath, particularly the filtrate flowpath, of a dispense cassette into a dispense container prior to the outer container or bag being opened.

Piercing device 210 includes a needle holder 212, a piercing guide 214, and a vial collar 216. Needle holder 212 maintains the fill needle in place and enables fluid connection between filtrate flowpath 98 of cassette 100 and cavity 3 of container 1. Piercing guide 214 holds the fill needle away from the stopper until moved to the second position, and also guides the fill needle for a proper septum piercing. Vial collar 216 ensures the device is tightly connected onto the top of the sterile vial (of container 1). Needle holder 212 is shown with a fill needle 18 fixed to extend therethrough in overlying registry with septum 7 of container 1. In a first position, needle holder 212 maintains needle 18 in spaced separation from septum 7. As also shown, needle holder 212 may be moved along piercing guide 214 to a second position, such that the free end 18*a* of needle 18 pierce through septum 7 so as to extend into cavity 3 of container 1.

Piercing guide 214 and vial collar 216 may be formed either as separate components which are mated together, or as a single component which provides both functions. When formed as separate components, the present invention contemplates both piercing guide 214 and vial collar 216 may be removable from container 1 so that, after filling, container 1 will be free of all components of the present invention. Alternatively, vial collar 216 may remain with container 1 after is removed therefrom. Vial collar 216 may thus be removably snapped into position about neck 4 of container 1 by deflection of vial collar 216. Similarly, when piercing guide 214 is not affixed to vial collar 216, piercing guide 214 may be removably attached thereto by means such as an interference fit, a bayonet-type connection, threaded connection, etc. Desirably, the present invention contemplates that needle holder 212 will be affixed to piercing guide 214 so that needle holder 212 would be removed from container with piercing guide 214, whether with vial collar 216 or not. That is, the present invention contemplates that it will be far easier to remove either piercing guide 214 from vial collar 216 or vial collar 216 from the neck of the container than to remove needle holder 212 from piercing guide 214.

Needle holder 212 includes an elongate needle holder body 230 having opposed closed end 232 and open end 234 and an open cylindrical wall 236 extending therebetween. Cylindrical wall 236 defines needle aperture 238 opening on open end 234. Closed end 232 includes transversely-extending needle surface 240. Surface 240 defines needle receptor 242. Needle receptor 242 defines needle channel 246 for receiving fill needle 218. Desirably, needle receptor 242 include means for securely holding needle 18 with respect to body 230. By way of illustration and not of limitation, the means for securely holding needle 18 may be mechanical means which engages the needle, such as by interference fit or engagement mechanisms, or chemical means such as a suitable adhesive which secures needle 18 and/or its luer base 22. Luer base 22 of fill needle 18 is connected to dispense conduit 90 of dispense cassette 210.

Needle receptor 242 defines through-aperture 246 extending in open fluid communication with needle aperture 238. When fixed by needle receptor 242, needle 18 extends into and desirably through needle aperture 238. While needle 18 is shown to extend through aperture 238 and beyond open end 234 of needle holder 212, the present invention contemplates that the arrangement of needle holder 212, guide 214 and vial collar 216 with respect to each other such that the required penetration into or though needle aperture 38 of needle 18 may be appropriately varied. Cylindrical wall 236 includes an inwardly-facing cylindrical surface 250 and supports an inwardly extending detent 252 at open end 234. The present invention contemplates that detent 252 may be configured in a manner known in the art, such as an inwardly-extending annular rim or as a series of annularly-arrayed projections. As will be described hereinbelow, detent 252 will cooperate with a mating detent on the needle guide 214 so as to maintain needle holder in the first or second position as desired.

Piercing guide 214 includes a guide body 254 having an elongate cylindrical wall 526 extending between opposed first and second open ends 258 and 260, respectively. Wall 256 defines an open elongate guide passage 262 extending in open fluid communication between first and second open ends 258 and 260. Guide passage 262 is in fluid communication with needle aperture 38 and in underlying registry with through-apertures 246. Wall 256 includes an outer cylindrical surface 264 supporting mating detents 266 and 268 at first end 258 and second end 260, respectively. As previously described, mating detents 266 and 268 cooperate with detent 252 so as to maintain needle holder 12 in either the first or second position, as well as to allow an operator to move needle holder from the first position to the second position. Detents 266 and 268 are contemplated, like detent 252, to be either a single annular rim or an array of outwardly-extending projections. Furthermore, wall 256 may define an elongate linear channel extending between each of detents 266 and 268 so as to both ensure linear movement of needle holder 212 with respect to guide 214. Additionally, the present invention contemplates that needle holder 212 could support detents at opposed ends thereof, and piercing guide 214 only supports a single detent or array of detents at the first end thereof. Moreover, the present invention contemplates that both needle holder 212 and piercing guide 214 each support a pair of cooperating detents at both ends thereof to provide additional locking strength for maintaining needle holder 212 in the second position.

Vial collar 216 includes an annular collar body 255 defining a vial passageway 257 therethrough. Collar body 255 includes cylindrical wall 259, having an inwardly-facing cylindrical surface 261, extending between opposed first and second open ends 263 and 265. First open end 263 mates with second open end 266 of piercing guide 214. As previously noted, the present invention contemplates that vial collar 216 may be formed as a single unity with piercing guide 214 or as separate components which are either permanently fixed together. Additionally, vial collar 216 and piercing guide 214 may separably engage each other so that piercing guide 214 may be removed from engagement with vial collar 216. As shown in FIGS. 12 and 13, collar body 255 includes a first inwardly-extending annular rim 267 at first end 263. Rim 267 is configured to abut against the annular crimp 9 or with septum 7 of container 1. Additionally, cylindrical surface 261 supports an inwardly-extending annular detent 269 at second open end 271. Detent 269 engages the undersurface of annular rim 8 of container 1. Detent 269 is designed to deflect about rim 8 as vial collar 216 is positioned onto container 1. The present invention contemplates that detent 269 may take the form of a single annular rim, or an array of inwardly-extending projections, each of which will deflect sufficiently to be moveable past annular rim 8 as vial collar 216 is emplaced. Alternatively still, collar body 255 may include a number of axially-extending deflectable leafs on which the detents 269 are supported. The present invention contemplates that vial collar 216 may be removable from container 1 after a filling operation, or vial collar 216 may separate from device 210 so as to be transferable with container 1.

Needle holder 212 is thus movable from a first position, shown in FIG. 12, to a second position shown in FIG. 13. In the first position, detent 252 engages first detent 272 so as to maintain needle 18 away from septum 7 of container 1. In the second position, detent 252 is moved beyond detent 274 so as to extend and maintain needle 18 through septum 7. In the second position, fill needle 18 places cavity 3 in fluid communication with filtrate flowpath 98 of dispense cassette 75.

After fluid dispensing has been completed, needle 18 is retracted back through septum 7 and container 1 may be removed from device 210. As previously described, device 210 may either be removed from engagement with vial collar 216 or piercing guide 214 may be disconnected from vial collar 216. Device 210 has thus maintained septum integrity after attachment to container 1 until just prior to opening containment bag 102, when needle holder 212 has been moved to the second position so that needle 18 pierce septum 7. Filtrate flowpath 98 and cavity 3 will thus maintain the clean and sterile environment for dispensing a fluid into cavity 3. In this manner, device 210 provides a means for sterile dispensing in non-sterile environments.

Figure 14:
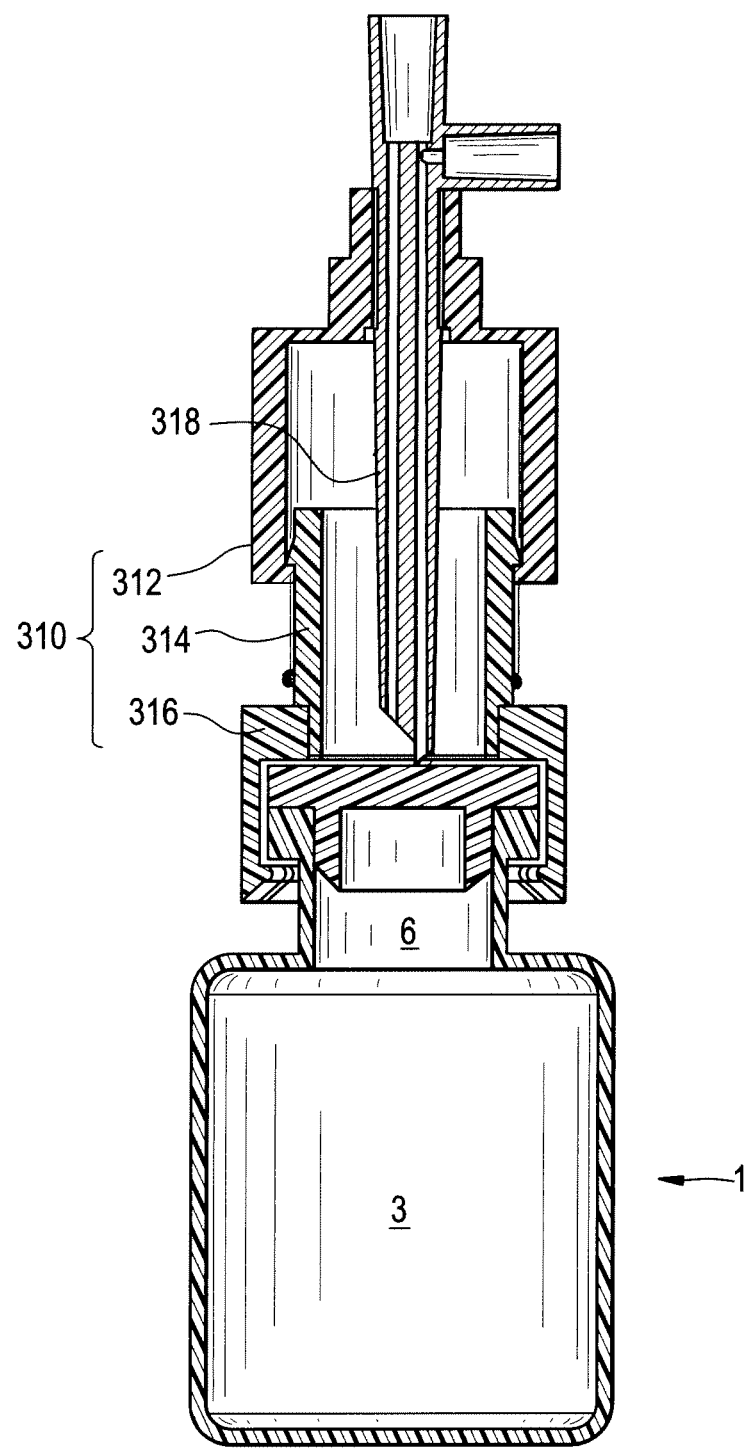
FIG. 14 depicts a dual-lumen needle piercing device of the present invention in the first, pre-pierced, position.
Figure 15:
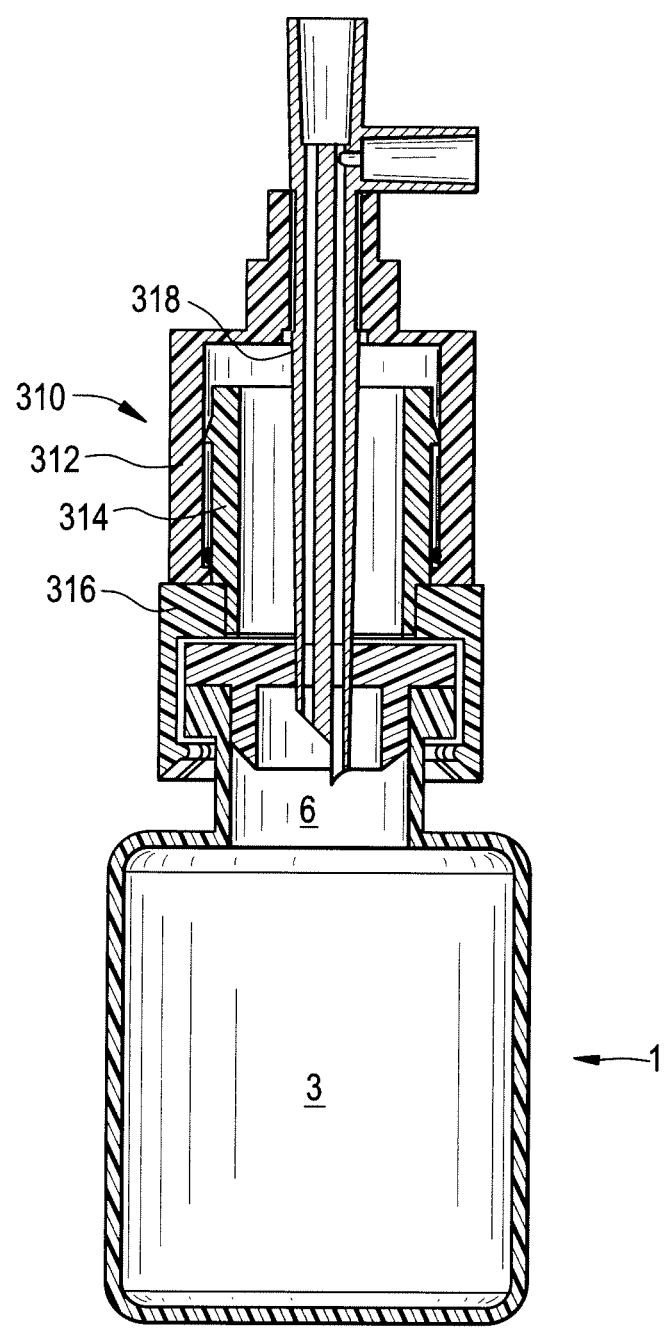
FIG. 15 depicts the piercing device of FIG. 14 in the second, piercing, position.

FIGS. 14 and 15 depict a dual-lumen needle piercing device 310 of the present invention in the first, pre-pierced, position and the second, piercing, position, respectively. Device 310 may be used when a dual-lumen needle is used to pierce septum 7 with a single puncture. The dual-lumen needle provides for both filling and venting of cavity 3. Dual-lumen needle 318 is shown in disproportionate scale with respect to septum 7, for simplicity of describing its design and operation. Dual-lumen needle is desirably sized to provide the same sized puncture as a 16-gage needle, so that septum integrity will be maintained after withdrawal of dual-lumen needle 318 when dispensing is complete. Thus, device 310 is configured similarly to device 210, in that it secures a single needle therein and provides a single puncture through septum 7, but this single needle provides both filling of container 1 and venting of gases during filling. Dual-lumen needle 318 provides two isolated fluid passages, one for the liquid dispensing product and one for vented gas.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A kit for dispensing radiopharmaceuticals, said kit comprising:
    a sealed container defining a container cavity;
    a dispense manifold comprising a manifold body defining an elongate fluid conduit, a filter at one end of said conduit, at least one valve located along said fluid conduit for selectably directing a fluid in said fluid conduit toward a first or second dispense conduit, each said first and second dispense conduit supporting a respective one of a first and second fill needle affixed to the end thereof;
    a connector cap for each said dispense conduit extending from said manifold, wherein each said dispense needle is held by the needle holder of its respective connector cap in the first position, and wherein the vial collar of each said connector cap is affixed to a vial such that the collar aperture is in overlying registry with the septum sealing its respective vial;
    wherein said dispense manifold and each said connector cap and vial are adapted to be held within the container cavity and wherein each said needle holder body of its respective connector cap is moveable from said first position to said second position while in said container, and wherein the connector cap comprises:
    a vial collar comprising a vial collar body defining a collar aperture to be positioned in overlying registry with the septum of the vial; and
    a needle holder comprising a needle holder body providing a means for holding one or more elongate needles in registry with the collar aperture, said needle holder body being moveable with respect to said vial collar between a first position spaced from said vial collar and a second position proximate said vial collar, such that the one or more needles held by said needle holder will puncture through the vial septum.

2. The kit of claim 1, wherein said container is a plastic bag.

3. The kit of claim 1, wherein said container further comprise a plastic tray formed to hold the manifold and each connector cap and vial.

4. The kit of claim 3, wherein said tray further comprises a deflectable blister adjacent to each needle holder so as to move the needle holder from the first position to the second position when the blister is deflected.

5. The kit of claim 1, wherein said manifold further comprises a pump mechanism for directing a fluid through the filter, through the fluid conduit, and into the vial.

6. The kit of claim 1, wherein said container cavity maintains a sterile environment therein while sealed.

7. The kit of claim 1, wherein the connector cap further comprises a non-movable piercing guide,
    wherein the needle holder body provides the means for holding the needle for movement through the piercing guide and in registry with the collar aperture, and
    wherein the needle holder body is configured to be affixed to the piercing guide once moved to the second position to enable removal of the needle holder from the vial with the piercing guide.

8. The kit of claim 7, wherein the piercing guide comprises an annular guide body positioned between said vial collar and said needle holder, said guide body defining a guide cavity in fluid communication with said collar aperture.

9. The kit of claim 8, wherein said guide body is affixed to said vial collar.

10. The kit of claim 8, wherein said guide body is removably attached to said vial collar.

11. The kit of claim 1, wherein said vial collar is removably attachable to the vial.

12. The kit of claim 1, wherein said needle holder holds a first and a second needle spaced from the septum when in the first position and wherein both said first and said second needles extend through the septum in the second position.

13. The kit of claim 1, further comprising a locking mechanism for maintaining said needle holder in said second position with respect to said vial collar.

14. The kit of claim 7, further comprising a locking mechanism so as to maintain said needle holder in said second position with respect to said piercing guide.

15. The kit of claim 1, further comprising cooperating detent locks for releasably holding said needle holder in said first position.

16. The kit of claim 15, wherein said cooperating detent locks are located on said vial collar body and said needle holder.

17. The kit of claim 15, wherein said cooperating detent locks are located on at least said needle holder body.

* * * * *